(12) United States Patent
Bombardelli

(10) Patent No.: US 7,691,422 B2
(45) Date of Patent: Apr. 6, 2010

(54) ORAL COMPOSITIONS FOR THE TREATMENT OF CELLULITE

(75) Inventor: Ezio Bombardelli, Groppello Cairoli (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 10/570,943

(22) PCT Filed: Sep. 10, 2004

(86) PCT No.: PCT/EP2004/010148

§ 371 (c)(1),
(2), (4) Date: Mar. 8, 2006

(87) PCT Pub. No.: WO2005/027947

PCT Pub. Date: Mar. 31, 2005

(65) Prior Publication Data

US 2006/0292249 A1 Dec. 28, 2006

(30) Foreign Application Priority Data

Sep. 19, 2003 (IT) .......................... MI2003A1789

(51) Int. Cl.
*A61K 36/87* (2006.01)
*A61K 36/16* (2006.01)
*A61K 36/00* (2006.01)

(52) U.S. Cl. .................. 424/776; 424/752; 424/725

(58) Field of Classification Search .................. None
See application file for complete search history.

(56) References Cited

U.S. PATENT DOCUMENTS

2007/0020349 A1    1/2007   Bombardelli

FOREIGN PATENT DOCUMENTS

| EP | 0 275 224 A2 | 7/1988 |
| EP | 0275005 | * 7/1988 |
| EP | 0 283 713 A2 | 9/1988 |
| WO | WO 01/78674 A1 | * 10/2001 |
| WO | WO 02/092042 A2 | 11/2002 |

OTHER PUBLICATIONS

Bedi et al. Herbal Therapy in Dermatology; Arch Dermatol., vol. 138, Feb. 2002, pp. 232-242.*
Mahady, G. Ginkgo Biloba for the Prevention and Treatment of Cardiovascular Disease: A Review of the Literature; J. Cardiovasc. nurs, 2002; 16(4), pp. 21-32.*
Ackerson, A. Get a Leg Up; Better Circulation is no Mean Feat; Better Nutrition, Atlanta, May 2003, vol. 65, Iss. 5, p. 79, pp. 1-3 of ProQuest.*
McGovern, T. Botanical Briefs: The Ginkgo Tree—Ginkgo Biloba L.; Cutis, Chatham, Sep. 1999, vol. 64, Iss. 3, p. 154-157, pp. 1-3 of ProQuest.*
Thomas, D. Cellulite Solution Still Draws Debate; More Than Just Fat; Omaha World-Herald, Omaha, Nebraska, Dec. 13, 1999, p. 33, pp. 1-4 of ProQuest.*
Moyer: Oral Supplement Combo Improves Cellulite, Striae; Dermatology Times, Apr. 2004; 25, 4, p. 70.*
VascularWeb: Chronic Venous Insufficiency; online URL:<http//www.vascularweb.org/patients/NorthPoint/Chronic_Venous_Insufficiency.html. accessed Nov. 17, 2008, pp. 1-3.*

* cited by examiner

*Primary Examiner*—Patricia Leith
(74) *Attorney, Agent, or Firm*—Porzio, Bromberg & Newman, P.C.

(57) ABSTRACT

The present invention relates to oral pharmaceutical and cosmetic compositions for the treatment of cellulite containing *Vitis vinifera* extracts, *Centella asiatica* triterpenes and dimeric *Ginkgo biloba* flavonoids, in the free form or complexed with phospholipids.

1 Claim, No Drawings

ORAL COMPOSITIONS FOR THE TREATMENT OF CELLULITE

The present invention relates to oral pharmaceutical and cosmetic compositions containing ingredients of vegetable origin for the treatment of cellulite.

More particularly, the present invention relates to pharmaceutical and cosmetic oral compositions for the treatment of cellulite containing *Vitis vinifera* extracts, dimeric *Ginkgo biloba* flavonoids and *Centella asiatica* triterpenes as the active ingredients.

According to the present invention, the active ingredients are in the free form or complexed with phospholipids.

Cellulite affects a remarkable and increasing percentage of the western population, especially women, including many adult women with normal body weight not affected by obesity. Cellulite is related to a condition of panniculopathy, characterized by poor peripheral circulation, oedema, fibrosis and altered lipocytes metabolism, and an ideal treatment should take into account all these aspects.

A number of pharmaceutical or cosmetic compositions for the treatment of cellulite are presently available on the market: they are generally based on active principles of vegetable origin, such as ivy, horse-chestnut or kola tree (*Centella asiatica*) extracts, caffeine, beta-adrenergic stimulants, methylxanthines and the like. However, none of them has proved really effective so far and the improvements are often due to the diet regimen generally associated with the use of the compositions, rather than to the compositions themselves.

It has now been found that oral pharmaceutical and/or cosmetic compositions containing a combination of active principles of vegetable origin, which are object of the present invention, allow to obtain optimal results in the treatment of cellulite, significantly reducing the deposits of subcutaneous fat and "orange peel" skin, thanks to the combination of the different activity of the various components, which exert antioedema, antiphosphodiesterasis and vasokinetic activity, and promote collagen production. The compositions of the invention have also proved effective in the treatment of venous insufficiency of the lower limbs.

All the active principles of the compositions of the invention are known and used in pharmaceuticals and/or in cosmetics; however, it should be noted that the compositions show a synergistic effect and that the activity of the single actives used separately is by far lower than that of the actives used in combination.

The compositions of the present invention can contain from 10 to 500 mg per dose unit of *Vitis vinifera* standardized extracts, from 10 to 500 mg of dimeric *Ginkgo biloba* flavonoids and from 10 to 500 mg of *Centella asiatica* or an equivalent amount of the corresponding phospholipid complexes.

Components a)-c) in the free form are commercially available.

Phospholipid complexes of *Vitis vinifera* standardized extract (also referred to as "components a") are disclosed in European Patent 275.224. Said extract, consisting of the poliphenols fraction contained in *Vitis vinifera* seeds, contains gallic acid, catechin and epicatechin monomers, dimers, trimers, tetramers, pentamers, hexamers and eptamers in the free form or esterified with gallic acid.

In vitro and in vivo studies have demonstrated the high antioxidant activity of the extract (from 10 to 200 times higher than that of vitamin E, depending on the experimental model), which allows to eliminate the most reactive radical species and counteract their harmful effects. Moreover, the extract is able to inhibit xanthine-oxidase and chelate $Cu^{++}$ and $Fe^{+++}$, thus preventing enzyme-catalysed production of free radicals in tissues. Last, the *Vitis vinifera* extract inhibits collagenase and other proteases, thereby protecting the connective tissue and the skin from the noxious action of proteolytic enzymes released upon UV irradiation and in the course of inflammatory responses in the skin; moreover, the extract has selective affinity for the skin and circulatory structures, such as microvessels and capillaries, thus also exerting a protective action on the circulatory apparatus.

The complexes of dimeric *Ginkgo biloba* flavonoids with phospholipids (also referred to as "components b"), disclosed in EP 0 275 005, have the same activity of *Ginkgo biloba* flavones dimers in the free form, but induce a more prolonged release of the active principles and have a better bioavailability. *Ginkgo biloba* flavonoids dimers are extremely potent vasoactive agents due the fact that they inhibit the release of histamine and cAMP phosphodiesterase from mast cells. In particular, the inhibition of cAMP phosphodiesterase causes an increase of cAMP levels; since cAMP is able to activate lipocytes metabolism, these complexes exert a lipolytic action and improve microvascular perfusion and cutaneous trophism.

Phospholipid complexes of *Centella asiatica* standardized extract (also referred to as "components c") are disclosed in EP 0 283 713. This extract consists of a 4:3:3 mixture of three different molecules endowed with high activity on collagen metabolism: asiaticoside, asiatic acid and madecassic acid. These molecules improve the fibroblasts uptake of amino acids, mainly L-proline and L-hydroxyproline, which are the most important amino acids in collagen structure, both from the qualitative and quantitative standpoint. An improved collagen biosynthesis involves a faster replacement of degraded old fibres with new ones.

The compositions of the present invention will be administered orally, in the form of suitable formulations, either liquid (such as syrups, solutions, suspensions) or solid (such as tablets, sugar-coated pills, capsules, chewable tablets). The formulations will be prepared according to conventional methods, such as those disclosed in "Remington's Pharmaceutical Handbook", Mack Publishing Co., New York, USA, using suitable excipients.

Examples of compositions according to the invention are reported hereinbelow.

EXAMPLE I

Tablet

| Phospholipids complex | |
| --- | --- |
| *Vitis vinifera* extract | 240 mg |
| Phospholipid complex of dimeric *Ginkgo biloba* flavonoids | 100 mg |
| Phospholipid complex of *Centella asiatica* triterpenes | 60 mg |
| Sodium croscaramellose | 28 mg |
| Silicon dioxide | 8 mg |
| Talc | 4 mg |

EXAMPLE II

| | |
|---|---|
| *Vitis vinifera* extract | 150 mg |
| *Ginkgo biloba* dimeric flavonoids | 100 mg |
| *Centella asiatica* triterpenes | 10 mg |
| Dihydrate dicalcium phosphate | 150 mg |
| Microcristalline cellulose | 100 mg |
| Croscaramellose sodium | 28 mg |
| Silicon dioxide | 8 mg |
| Magnesium stearate | 9 mg |
| Talc | 3 mg |

The invention claimed is:

1. A method for the treatment of cellulite comprising orally administering a composition to a subject presenting with cellulite; wherein said composition comprises:

a) *Vitis vinifera* standardized extract;

b) dimeric *Ginkgo biloba* flavonoids; and c) *Centella asiatica* triterpenes;

in admixture with conventional excipients and carriers;

wherein components a) b) and c) are in the form of complexes with phospholipids.

\* \* \* \* \*